United States Patent [19]

Johannsson

[11] Patent Number: 4,668,639
[45] Date of Patent: May 26, 1987

[54] BIOCHEMICAL DETECTION METHOD AND KIT FOR USE THEREIN

[75] Inventor: Axel Johannsson, Cambridge, England

[73] Assignee: IQ (BIO) Limited, Cambridge, England

[21] Appl. No.: 625,253

[22] Filed: Jun. 27, 1984

[30] Foreign Application Priority Data

Jun. 30, 1983 [GB] United Kingdom ............... 8317855

[51] Int. Cl.⁴ ................. G01N 33/566; G01N 33/543
[52] U.S. Cl. .................................. 436/518; 436/501; 436/825; 436/826; 435/810
[58] Field of Search ............ 436/501, 518, 536, 538, 436/534, 825, 826; 435/810

[56] References Cited

U.S. PATENT DOCUMENTS 4,060,597 11/1977 Sato et al. ........................... 436/534
4,256,724 3/1981 Rutner et al. ................... 436/532 X
4,319,882 3/1982 Sharma ............................. 424/11 X Primary Examiner—Sidney Marantz
Assistant Examiner—Jack Spiegel
Attorney, Agent, or Firm—Cushman, Darby & Cushman

[57] ABSTRACT

A biochemical detection method in which a ligand is bound to a surface, an aqueous solution containing an antiligand is brought into contact therewith whereby antiligand becomes bound to ligand, the aqueous solution is separated from the thus bound antiligand, and the antiligand is detected using a detection means associated therewith, for example using amplified enzyme-linked immunoassay. The surface is treated with at least one agent for limiting non-specific binding of either the ligand or the antiligand with other substrates, which agent is (i) a surfactant containing an aromatic residue and having an HLB number of at least 16,
(ii) a zwitterionic surfactant, or
(iii) a solution containing a salt of a polyvalent anion, in a concentration of at least 100 mM.

Preferably, all three agents are used simultaneously. The three agents may be used during the detection procedure in solutions containing the antiligand, in washing solutions used during the method, or in solutions used to pre-treat the plate.

17 Claims, No Drawings

BIOCHEMICAL DETECTION METHOD AND KIT FOR USE THEREIN

This invention relates to biochemical detection methods, in which a ligand is bound to a surface, and an antiligand becomes bound to the said ligand.

The term ligand and antiligand are used herein to denote a complimentary pair of substances which are capable of recognizing the specific spatial and charge configuration of each other, and of binding specifically with each other. Examples of ligands are, for example antigens, haptens, and the partners of cell and non-cell associated, non-antibody receptors. The term "antiligand" includes, for example, antibodies and non-cell and cell-associated non-antibody receptors. The term "non-antibody" receptors as used herein includes non-antibody receptors obtained from natural sources, and those produced synthetically, or semi-synthetically, and also includes analogues thereof that are capable of binding to an appropriate partner. Simiarly, their respective partners may be obtained from natural sources, or may be synthetic, or semi-synthetic, or analogues of natural partners, provided that they are capable of binding to the appropriate receptor.

A large number of examples of ligand/antiligand pairs are given in U.S. Pat. No. 4,446,231, all of which should be considered to be incorporated herein by reference.

Many biochemical detection methods employ the interaction between a ligand and an antiligand to bring about the placement of the antiligand in a position where it may be detected by some signal generating means. The ligand is bound to a surface by chemical (covalent linkage) or physiochemical (hydrophobic interaction, adsorption, ligand-antiligand interaction or the like) means and the antiligand is normally introduced in aqueous solution. Antiligand present in the solution binds to the ligand. Separation of the solution from the surface will then leave antiligand bound with the surface (via its binding with the ligand). An assay for the antiligand may then be carried out.

Generally the assay is carried out with the antiligand bound to the surface, although sometimes it may be first unbound from the surface.

Such placement of antiligand is widely employed in assay techniques for various proteins. The signal generating means may take the form of so-called "enzyme linked immunoassay", radioimmunological, immunobioluminescent, or immunofluorescent methods. A number of such techniques are disclosed, for example, in U.S. Pat. No. 4,446,231, the disclosure of which is incorporated herein by reference.

It is known that the binding of antiligands to a surface can be affected by the use of certain surfactants, and in particular TWEEN 20 (Trade Mark) (a sorbitan monolaurate detergent) has been employed in known detection methods.

In any biochemical detection method, so-called "noise" can arise due to non-specific binding between various components present in the system. Examples are binding of the antiligand to various proteins present in the system, other than the ligand bound to the surface, binding of the antiligand to the wall of the vessel in which the method is carried out, and binding of the ligand bound to the surface of the vessel with the antiligand, in a non-specific way, i.e. other than to its intended binding side. Such non-specific binding within biochemical detection systems is particularly significant when the detection means employs an amplification system, for example the enzyme-linked system described above.

We have now discovered that certain agents are effective to substantially reduce non-specific binding in biochemical detection methods of the aforesaid kind, and that such agents can be employed in the solution containing the antiligand, in any solution with which the surface having the bound ligand is subsequently treated, or in a solution used in the preparation of the surface having the ligand bound to it.

Accordingly, in a first aspect of the invention, there is provided a biochemical detection method in which a ligand is bound to a surface, an aqueous solution containing an antiligand is brought into contact therewith whereby antiligand becomes bound to ligand, the aqueous solution is separated from the thus bound antiligand, and the antiligand is detected using a detection means associated therewith, characterized in that the surface is treated with at least one agent for limiting non-specific binding of either the ligand or the antiligand with other substances, which agent is (i) a surfactant containing an aromatic residue and having an HLB number of at least 16, (ii) a zwitterionic surfactant, or (iii) a solution containing a salt of a polyvalent anion, in a concentration of at least 100 mM.

The surfactant containing an aromatic residue preferably contains a hydrophilic substituent containing at least 10 carbon atoms, more preferably at least 20 carbon atoms. This hydrophilic substituent will contain hydrophilic groups such as ether linkages and/or hydroxyl groups. It is preferred that the hydrophilic substituent is an oxyethylene condensate, containing at least 20 oxyethylene residues.

Preferred surfactants of the type (i) are surfactants of the formula $Ar\text{-}(OCH_2CH_2)_n\text{-}OA$, wherein Ar is a phenyl group optionally substituted by one or more alkyl groups containing in total from 1 to 14 carbon atoms, n is from 20 to 100, and A is a hydrogen atom, or a methyl or ethyl group. Most preferably, Ar is a phenyl group substituted by an alkyl group containing from 4 to 12 carbon atoms, particularly a phenyl group substituted by an alkyl group containing 8 carbon atoms. A is preferably hydrogen. n preferably has a value of from 25 to 80, for example 40, 50, 60, or 70.

Particularly favourable surfactants of this type may be represented as para-octyl-phenyl-$(OCH_2CH_2)_n$OH, wherein n is as described above. A series of suitable surfactants of this kind are those sold under the designation TRITON X-405, X-705 etc., by the Sigma Chemical Company, the designations "405" and "705" indicating a mean ethoxy chain length of 40 and 70 respectively.

TRITON X-405 and X-705 have HLB ratio of 17.9 and 18.7 respectively (as defined by Griffin, W.C. (1949) J. Soc. Cosmet. Chem., 1, 311–316). It is particularly preferred that the aromatic-containing surfactants have an HLB ratio of at least 16, preferably at least 17, although it may be that other detergents having a structure as set forth above, but having a lower HLB number, are satisfactory.

The aromatic detergent is preferably used in an aqueous solution, preferably an aqueous buffer solution, in which the concentration of the detergent (i) is from 0.01% to 10%, more preferably from 0.05% to 1% by weight.

The agent of type (ii) for reducing non-specific binding is a zwitterionic surfactant, preferably one having one amino residue and one acidic residue, which may be for example a carboxylic, phosphoric, or sulphonic acid residue. Preferably, the zwitterionic surfactant will have one tertiary amino group, and one sulphonic acid group.

Suitable zwitterionic surfactants are ones of the formula $R^1R^2NR^3R^4$ wherein $R^1$ and $R^2$ are each independently hydrogen or a $C_1$–$C_6$ alkyl group, $R^3$ is a $C_1$–$C_6$ alkyl group bearing an $SO_3$ substituent, and $R^4$ is a $C_8$–$C_{22}$ alkyl group. Preferably, $R_1$ and $R_2$ are each methyl or ethyl, more preferably, methyl. $R_3$ may be a $C_2$–$C_6$, preferably $C_3$–$C_4$, more preferably $C_3$ alkyl group, bearing an $SO_3H$ substituent group.

$R^4$ may be a $C_{10}$ to $C_{18}$, preferably $C_{12}$ to $C_{16}$, more preferably $C_{14}$ alkyl group.

In a particularly preferred embodiment, $R_1$ and $R_2$ are each methyl, $R_3$ is $CH_2CH_2CH_2SO_3H$, and $R_4$ is n-tetradodecyl. A example of a suitable detergent of this kind is that sold under the designation SB-14 by Calbiochem.

The zwitterionic surfactant is preferred employed in the form of an aqueous, preferably buffered solution, in a concentration of from 0.01% to 10% preferably from 0.05% to 1% by weight. The agent (iii) is a solution containing a salt of a polyvalent anion, in a concentration of at least 100 mM. Suitable salts are any which do not interfere with the biochemical detection method being carried out, and ammonium sulphate has been found to be particularly useful.

The salt is employed in a concentration of at least 100 mM, preferably from 200 to 800 mM, more preferably from 300 to 600 mM, particularly about 400 mM. The use of high concentrations of salts is of particular value in conjunction with one or both of the agents i or ii mentioned above.

The zwitterionic surfactant has been found to be of particular value when the surface to which the ligand is bound is a cellulosic surface, such as cellulose nitrate or nitrocellulose. Furthermore, the use of a zwitterionic surfactant produces particularly great and surprising advantages when the method of this invention is adapted to the detection of nucleic acids.

The beneficial effects of using a surfactant containing an aromatic residue and at least 20 oxyethylene residues are particularly pronounced when the surface to which the ligand is bound is a synthetic polymer (as opposed to a cellulosic material which is derived from a natural product), such as polystyrene, polyvinyl chloride, polyamide, polyester or the like, particularly when the surface is polystyrene.

The use of both the zwitterionic and aromatic-containing surfactants has been found to improve results still further.

The method of this invention is particularly useful when the antiligand is a phosphatase or a conjugate of a phosphatase. In such methods, the detection means may employ dephosphorylation of an aromatic phosphate such as para-nitrophenyl phosphate in a conventional manner. Preferably however the method described in European Patent Specifications Nos. 82300714, 82304117, and U.S. Pat. No. 4,446,321 may be employed.

The detection of the antiligand may be carried out either directly or indirectly, for example by measuring the effect of the antiligand on a second ligand/antiligand interaction. Differencing techniques may also be used.

In one preferred aspect, the invention provides a biochemical detection method in which a ligand is bound to a surface, an aqueous solution containing an antiligand which is a conjugate of a phosphatase is brought into contact therewith whereby the antiligand becomes bound to ligand, the aqueous solution is separated from the bound antiligand and the antiligand is detected by causing the dephosphorylation of a phosphate of a nicotinamide dinucleotide to produce nicotinamide dinucleotide which starts a cyclic chemical reaction whereby it and its reduced form are interconverted and a detectable change also occurs by operation of said cyclic chemical reaction, wherein an agent for limiting non-specific binding of the type (i), (ii), or (iii) as described above is utilized. The disclosures of the aforesaid to European Patent Specifications are incorporated herein by reference.

When this invention is adapted to the detection of a substance from the human or other mammalian body, it is often advantageous to use a sandwich technique. Thus, for example, when it is desired to detect an antigen (such as enzyme, protein, hormone, bacterial antigen, visual antigen or the like) from a human or other animal it is possible to obtain the biological fluid (such as blood, serum, urine or the like), immobilized the antigen suspected of being in said fluid therefrom by contacting the fluid with an antibody thereto which is bound to a surface. After incubating the surface and its bound antibody with the fluid, the fluid is separated from the surface and the surface washed. The antibody with the antigen then comprises the ligand referred to herein before which is bound to a surface. The antibody employed may be a polyclonal antibody or a monoclonal antibody.

In a further favoured form of this invention the fluid containing the antigen is added to a solution already in contact with the surface to which the ligand is bound. The antiligand can thus consist of antigen bound to labelled antibody (for example anti-antigen labelled with phosphatase) or antigen alone in which case a new ligand is formed which can subsequently react with the anti-ligand labelled antibody.

The method of the invention may be carried out utilizing a pre-prepared test kit, comprising a vessel containing a test liquid, having a surface to which a ligand is bound (preferably a multi-well test plate) and at least one further vessel containing a reagent solution. The agent for limiting non-specific binding may be incorporated within a solution in the kit, or may have been used to treat the surface of the first vessel before it is supplied.

Accordingly, in a further aspect of the invention, there is provided a biological test kit, comprising a first vessel for containing a test liquid, having a surface therein which is covered by the test liquid when in use, and having a first ligand adapted to bind with a corresponding anti-ligand bound to the said surface, a second vessel containing a reagent solution adapted to bind with anti-ligand bound with the said first ligand, and optionally, a vessel containing a washing solution for washing the said first vessel, characterized in that the reagent solution or the washing solution contains an agent for limiting non-specific binding of the antiligand and like substances, which is (i) a surfactant containing an aromatic residue and having an HLB number of at least 16, (ii) a zwitterionic surfactant, or (iii) a solution containing a salt of a polyvalent anion, in a concentration of at least 100 mM, or in that the said surface has been treated with such an agent during its preparation.

The invention is illustrated in the following Examples, all of which relate generally to immunoassay methods, and a general indication of a method of carrying out immunoassay techniques will first be described.

METHOD OF IMMUNOASSAY

Method of Preparing Coated Plate

The following is an example of an assay method which forms the basis with some variations of the method used in the following Examples.

Monoclonal antibodies against human chorionic gonadotrophin, (HCG), were obtained from Serono diagnostics (code 12/17 & 11/6). Polystyrene microtitre plates (Nunc immunoplate) were coated with antibody 11/6 by pipetting 0.10 ml of 5 mg/l solution in 200 mM sodium carbonate (pH 9.0) into each well of a plate, leaving overnight at room temperature, emptying the plate and washing 3 times by adding 0.25 ml of 0.5% bovine serum albumin (BSA), and 5% lactose, (pH 7.5). The plates were left to air dry before being used.

Method of preparation of conjugate and standards

A conjugate of alkaline phosphatase and the second monoclonal antibody (Serono 12/17) was made by thiolating the antibody and subsequently reacting it with a maleimide derivative of the alkaline phosphatase. Unreacted alkaline phosphatase and antibody were removed by high pressure gel filtration (TSK column SW 4000).

The conjugate was diluted to a concentration of approximately 1 ng/ml in a test buffer, containing 10 mM tris, (pH 7.5) 1 mM $MgCl_2$, 0.1% sodium azide and 1% BSA. Standard HCG solutions containing 0 and 1 mIU/ml were also prepared, in the same buffer. The effects of salts, and detergents on an immunoassay for HCG were determined by including the components of interest in the conjugate solution. All determinations were performed in duplicate and the average of resulting measurements used in all calculations.

Test Procedure 0.075 ml of conjugate were pipetted into coated wells of a microtitre plate followed by 0.025 ml of 0 or 1 mIU HCG standard. 0.075 ml of test buffer without conjugate followed by 0.025 ml of HCG standard were pipetted into wells for determination of reagent blank.

The plate was incubated at room temperature for 1 hour, the wells were emptied and washed four times with 0.25 ml of test buffer.

Remaining alkaline phosphatase was measured as follows. 0.1 ml of 0.1mM nicotinamide adenine dinucleotide phosphate, (NADP) in 50 mM diethanolamine (pH 9.5) were added and after a further 20 min 0.20 ml were added of a solution containing alcohol dehydrogenase, 0.2 mg/ml; diaphorase 0.15 mg/ml; p-iodonitrotetrazolium violet, 0.55 mM; ethanol, 4% (v/v); sodium hydrogen phosphate buffer, 25 mM pH 7.2. Colour development was stopped after a further 10 min by adding 0.050 ml of 0.2 M sulphuric acid. The absorbance of each well at 492 nM (A492 nm) was read in a Multiskan MC spectrophotometer through the well plate reader.

The signal in the assay is the difference in absorbance given by the wells originally containing the 0 and 1 mIU HCG standard, an conjugate solution.

The noise in the assay is the difference in absorbance between the 0 mIU and reagent blank.

EXAMPLE 1

The effect of addition of high concentrations of ammonium sulphate was tested as follows. Immunoassays were carried out in accordance with the above method. Three buffer solutions were utilised, the first with no additions, the second with the inclusion in the buffer of 400 mM $(NH_4)_2SO_4$, and third with the addition of 400 mM NaCl.

The noise and signal to noise ratio were measured for each case, and the results were as shown in Table 1.

TABLE 1

| Addition | Noise (A492 nm) | Signal to noise |
| --- | --- | --- |
| no addition | 2.112 | less than 0.1 |
| 400 mM $(NH_4)2SO_44$ | 0.052 | 2.5 |
| 400 mM NaCl | 0.78 | 0.2 |

It can be seen that the addition of 400 mM ammonium sulphate results in a dramtic increase in signal-to-noise ratio, both as compared with no salt addition, and as compared with the addition of a corresponding amount of sodium chloride.

EXAMPLE 2

This Example illustrates the effect of Triton X-405 and X-705 detergents in reducing non-specific binding of an alkaline phosphatase conjugate to a coated polystyrene test plate. Bovine IgG was used to coat a polystyrene plate as above, but at concentration of two micrograms per ml in 50 mM carbonate buffer, at pH 9.0, for 45 minutes. The plate was washed four times with a washing solution containing 10 mM phosphate buffer, 150 mM sodium chloride, and 0.1% detergent (Tween 20).

A conjugate was prepared from rabbit anti-human prostatic acid phosphatase (Miles) and alkaline phosphatase by incubation in phosphate buffered saline pH 7.2(PBS), containing 0.1% (v/v) glutaraldehyde at 20° C. for 4 hours. The conjugate was then diluted into PBS containing 0.1% BSA and 1 mM $MgCl_2$. Aliquots of this solution were added to a buffer containing PBS, 1 mM $MgCl_2$, and test additives as shown in Table 2, at four concentration levels for each test additives. Thus, 4 test solutions were provided for each of the five additives and a control containing no additives.

0.050 ml of each test solution were pipetted into wells of the coated plate, and incubated for 1½ hours at 20° C. The wells were then emptied, and washed 4 times with 0.25 ml of PBS containing 0.1% v/v detergent (Tween 20). Bound conjugate was measured colourimetrically as in Example 1. Because there is in this case no specific interaction between components of the assay, the increase in absorbance above the reagent blank was a measure of non-specific binding of the conjugate (i.e. noise).

The results are as shown in Table 2.

TABLE 2

| Sample | Conjugate Amount ng. | A495 | Noise |
|---|---|---|---|
| Control | 5 | .240 | 0.134 |
|  | 16 | .524 | 0.408 |
|  | 62.5 | 1.275 | 1.159 |
|  | 500 | 1.366 | 1.250 |
| 1% Triton X-100 | 5 | .155 | 0.039 |
|  | 16 | .330 | 0.214 |
|  | 62.5 | 0.851 | 0.735 |
|  | 500 | 1.319 | 1.203 |
| 1% Triton X-405 | 5 | 0.116 | 0.000 |
|  | 16 | 0.148 | 0.032 |
|  | 62.5 | 0.182 | 0.066 |
|  | 500 | 0.357 | 0.241 |
| 30% Butanol | 5 | 0.345 | 0.229 |
|  | 16 | 0.470 | 0.354 |
|  | 62.5 | 1.326 | 1.210 |
|  | 500 | 1.365 | 1.249 |
| Polyvinylpyrollidone (PVP) | 5 | .231 | 0.115 |
|  | 16 | .365 | 0.249 |
|  | 62.5 | .999 | 0.883 |
|  | 500 | 1.338 | 1.222 |
| Gelatine (30 mg/ml) | 5 | 0.124 | 0.008 |
|  | 16 | 0.543 | 0.427 |
|  | 62.5 | 0.574 | 0.458 |
|  | 500 | 0.789 | 0.673 |

It can be seen from the Figures in Column 4 that the presence of Triton X-405 in the reaction mixture significantly reduces the non-specific binding of the conjugate to the test plate. The various other additives, and in particular the lower molecular weight Triton X-100 have little effect on non-specific binding.

Example 2 was repeated using Triton X-705 detergent and Tween 20 detergent as additives. Triton X-705 gave a decrease in non-specific binding similar or better to that shown by Triton X-405. The results obtained using Tween 20 were similar to those obtained using Triton X-100, i.e. little or no reduction in non-specific binding.

EXAMPLE 3

This Example illustrates the use of Triton X-405 detergent in the preparation of the micro plate, and illustrates a reduction in non-specific binding similar to that obtained in Example 2.

A plate was prepared in a similar manner to the plate of Example 2. Twenty minutes before the plate was used, 0.1 ml of a 5% v/v aqueous solution of Triton X-405 was introduced into the wells. The plate was allowed to stand for 20 minutes at 20° C., and the excess was aspirated. A conjugate as in Example 2 (containing no additive) was added to the wells, and incubated for ½ hr at 20° C. The plate was then washed four times with a phosphate/saline buffer as in Example 2, and colorometric measurement was carried out as in Example 2. A control experiment was also provided with no pre-incubation with Triton X-405. The results are as shown in Table 3.

TABLE 3

| Sample | Amount of Conjugate in sample (ng) | A495 | Noise |
|---|---|---|---|
| Control | 5 | .276 | .106 |
| (No Triton X-405 in wells) | 20 | .738 | .662 |
| Pre-incubated with X-405 | 5 | .167 | .000 |
|  | 20 | .239 | .069 |
| Reagent blank |  | .170 |  |

It can be seen that the pre-incubation of the polystyrene surface with Triton X-405 provides a similar improvement in noise reduction as does the inclusion of Triton X-405 in the reaction solution.

EXAMPLE 4

Test solutions containing a conjugate as in Example 2 and different concentrations of Triton X-405 was prepared as in Example 2. The test solutions were allowed to stand for 1 hour, and thereafter 40 micro liter aliquots each containing 80 ng of conjugate were added to wells of a clean uncoated Nunc polystyrene test plate. The plate was incubated for 1 hr, washed three times with PBS, and the amount of conjugate bound to the plate was then measured as in Example 1. Since no protein had previously been bound to the plate, this is a measure of the extent to which Triton X-405 affects non-specific binding of a conjugate to polystyrene, rather than to protein bound to the plate. The absorbance and noise values obtained for the various concentrations are shown in Table 4.

TABLE 4

| Sample | X-404% (v/v) | A495 nm | Noise |
|---|---|---|---|
| Control | 0 | .598 | 0.528 |
| + Triton X-405 | 0.1 | .292 | 0.222 |
|  | 0.5 | .195 | 0.125 |
|  | .10 | .122 | 0.052 |
|  | .50 | .096 | 0.026 |
|  | 1.0 | .040 | 0.000 |
|  | 2.0 | .081 | 0.011 |
| Reagent blank |  | .070 |  |

It can clearly be seen from the noise produced for the various concentrations that the addition of Triton X-405 significantly reduces non-specific binding or "noise".

EXAMPLE 5

The effectiveness of various detergents in reducing noise in an assay as in Example 1 was assessed. A polystyrene test plate was prepared as in Example 1, and immunoassays carried out in accordance with the general method described above.

The effect of various detergents on reducing nonspecific binding was investigated, by including 0.1% v/v of various detergents in the conjugate solution. The detergents used were as follows:

A. (Triton X-705, a polyoxyethylene p-t-octyl phenol detergent, product by Sigma Chemical Company—HLB number 18.7).
B. Triton X100 (as A—HLB No. 13.5).
C. Triton X405 (as A—HLB No. 17.9).
D. Triton N101 (as A—HLB No. 13.4).
E. Calbiochem SB-14 (A zwitterionic detergent, 3-(Tetradecyldimethylammonium)-1-propanesulphonate).
F. Chaps (a zwitterionic detergent (3-[(3-cholamidopropyl)dimethyl-ammonia]-1-propane-sulphonate)).
G. Tween 20 (soribitan mono-laurate),—HLB number 16.7.
H. Lubrol LX (an ethylene condensate of a fatty acid.

The conjugate solution also contained 400 mM ammonium sulphate.

The noise and signal-to-noise ratio were determined as above, and the results are shown in Table 5.

TABLE 5

| Additive | Noise | Signal to noise |
|---|---|---|
|  | 0.052 | 2.5 |

TABLE 5-continued

| Additive | Noise | Signal to noise |
|---|---|---|
| Tween 20 | 0.068 | 2.1 |
| Triton X100 | 0.109 | 1.4 |
| Triton N101 | 0.126 | 1.0 |
| CHAPS | 0.051 | 3.0 |
| Triton X405 | 0.045 | 3.1 |
| Triton X705 | 0.015 | 8.6 |
| Lubrol LX | 0.093 | 1.2 |

EXAMPLE 6

The effect of SB14 in improving the detection of antibody to cholera toxin was investigated as follows.

A Linbro polystyrene microtitre plate was coated with cholera toxin by overnight incubation with toxin solutions of different combinations in carbonate buffer. The plate was emptied and the wells were washed three times with 0.25 ml of a solution containing 5% (w/v) lactose, 0.5% (w/v) BSA, 0.1% Triton X705, pH 7.5. An anti-toxin antibody standard was prepared by adding 0.01 ml of commercial rabbit anti-toxin antibody to 10 ml of a standard buffer containing Tris/HCl, pH 7.5, 50 mM; 3% (w/v) BSA; 0.1% Triton X705. 0.080 ml of anti-toxin anti-body standard or the standard buffer alone were added to the plate and incubated for ½ hr at 37° C. The plate was then emptied and washed three times with the standard buffer. 0.080 ml of conjugate (anti-rabbit-alkaline phosphatase, commercially available 1/1000 dilution in buffer the standard buffer or the standard buffer +0.1% SB 14) was pipetted into the wells and incubated for 1 hr at 37° C. Controls without conjugate were also included. The plate was emptied and washed as before and bound conjugate measured as in Example 1. Table 6A shows the absorbances obtained (mean of duplicates).

TABLE 6A

| Toxin Conc. (mg/l) | No SB 14 | | SB 14 added | |
|---|---|---|---|---|
| | with anti-toxin (signal + noise) | without anti-toxin (noise) | with anti-toxin (signal + noise) | without anti-toxin (noise) |
| 5 × 10⁻³ | 2.772 | 1.123 | 2.406 | .313 |
| 5 × 10⁻⁴ | 1.953 | .819 | 1.045 | .205 |
| 5 × 10⁻⁵ | 1.232 | .454 | .540 | .129 |
| 0 | .478 | .531 | .180 | .253 |

Table 6B shows the resulting signal to noise ratio at different toxin coating concentrations with and without SB14 added.

TABLE 6B

| Toxin Conc. | Signal to noise | |
|---|---|---|
| (ug/ml) | No SB-14 | SB 14 added |
| 5 × 10⁻³ | 1.46 | 6.69 |
| 5 × 10⁻⁴ | 1.38 | 4.09 |
| 5 × 10⁻⁵ | 1.71 | 3.19 |

EXAMPLE 7

Detection of progesterone in milk can be used as a marker for oestrus in cattle. The milk contains large amounts of alkaline phosphatase which binds non-specifically to polystyrene surfaces. This Example illustrates that such non-specific binding may be lowered using the method of the invention. A conjugate was prepared of 17 alpha-hydroxy progesterone and alkaline phosphatase. Samples were prepared of the conjugate and various additives as shown in Table 7. SB-12 and SB-16 are the dodecyl and hexadecyl homologues of SB-14.

0.01 ml of milk from normal Fresian cows was added to 0.2 ml of each sample in a clean NUNC polystyrene microtitre plate, and the plate was incubated at 22° C. for 3½ hours. The wells were then washed four times with a buffer containing 100 mM Tris (pH 8.5), and 0.1% Triton X-705. Remaining alkaline phosphatase activity measured as in Example 1.

The noise readings were averaged over 8 readings, and results are shown in Table 7.

TABLE 7

| Buffer Composition | 495 nM | Noise |
|---|---|---|
| 1. 100 mM Triethanolamine pH 7.5 200 mM Ammonium sulphate 0.1% Triton X-705 | .432 | .300 |
| 2. As 1 with the addition of 0.1% SB-14 | .184 | .052 |
| 3. As 1 with the addition of 0.1% SB-16 | .207 | .075 |
| 4. As 1 with the addition of 0.1% SB-12 | .270 | .138 |
| 5. Blank reading | .132 | |

SB 12 and SB 16 and, to an even greater extent, SB-14 are clearly capable of preventing contaminating alkaline phosphatase binding to a polystyrene surface. They thus reduce noise in an ELISA system for measuring progesterone in milk.

EXAMPLE 8

A test kit was prepared comprising a test plate and bottles containing the following:
1. NADP (0.001 mmoles: freeze-dried).
2. Substrate diluent: 10 ml of diethanolamine buffer, 50 mM, pH 9.5 containing 1 mM Mg Cl₂ and 0.1% sodium azide.
3. Amplifier: 4 mg alcohol dehydrogenase and 3 mg diaphorase, freeze-dried.
4. Amplifier diluent: 20 ml of sodium phosphate buffer, 25 mM, pH 7.2, containing 0.55 mM p-iodonitrotetrazolium violet and 4% ethanol.
5. Stopping solution: 0.2 M sulphuric acid.
6. Washing buffer concentrate: 1.2 M ammonium sulphate, 120 mM Tris, pH 8.0, 0.2% Triton X-705, 0.2% SB-14 and 0.1% sodium azide.
7. Conjugate: 9 ml of 400 mM ammonium sulphate, 0.1% Triton X-705, 0.1% SB-14, 8% BSA, 100 mM Tris, pH 7.5, 1 mM MgCl₂, 0.1 mM ZnCl₂, 10% new born calf serum, 0.1% sodium azide, a 1/3000 dilution of conjugate prepared as in Example 1, using a monoclonal antibody against TSH (Serono, D88).

The coated plate was prepared as in Example 1, except that the antibody was a monoclonal antibody against TSH (Serono, D49 2 mg/l) and the washing solution contained degraded gelatine (a solution of 0.5% BYCO (CRODA GELATIN), 0.05% TWEEN 20, and 0.01% thiomersal) in place of BSA. When dry, the plate was sealed in a foil bag containing a silica gel desiccant. Using a kit as described above, the TSH concentrations of 42 human serum samples were measured as follows:

0.075 ml of conjugate were pipetted into each well of the coated plate. 0.025 ml of six different TSH standards and 42 serum samples were added to the wells in duplicate, and the plate was incubated at 25° C. for two hours. Washing buffer was prepared by adding 132 ml of distilled water to the washing buffer concentrate. The plate was emptied, and each well was washed four times with 0.25 ml of the above buffer using an eight channel multipipette. The NADP was dissolved in the substrate diluent, and 0.10 ml were added to each well. The plate was incubated for 20 minutes at 25° C. The amplifier was dissolved in the amplifier diluent, and 0.20 ml added to each well. The plate was incubated for 10 minutes at 25° C. Colour development was stopped by adding 0.050 ml of stopping solution. The absorbance of each well at 492 mm was measured in a multiscan MC spectrophotometer. A calibration curve was constructed by plotting absorbance against the TSH concentration of the standards, and the TSH concentrations of the serum samples were thus determined by comparison with the calibration curve.

EXAMPLE 9

Biotinylated DNA was prepared using a Nick Translation Kit (EnZO Biochem Inc.) according to the manufacturer's instructions. Amounts of the biotinylated DNA as shown in Table 8 were transferred to discs (about 5.5 mm diameter) of nitrocellulose (Schleicer and Schull) and incubated for 2 hours at -80° C. An avidin-alkaline phosphatase conjugate (Sigma Chemical Company) was used to measure the amount of biotinylated DNA on the filters as follows:

A test buffer was made up containing 1 M NaCl, 50 mM triethanolamine, pH 7.5, 1 mM $MgCl_2$, 0.1 mM $ZnCl_2$, 0.05% sodium azide, both with and without 0.2% SB-16. Discs were preincubated in test buffer for 1 hour at 35° C., then transferred to conjugate made up into buffer at 1 mg/l protein, and incubated a further 20 minutes at 35° C. Each disc was then washed four times in 1 ml of test buffer at 35° C. The discs were then transferred to a clean microplate and alkaline phosphatase was determined as in Example 1.

Table 8 shows the absorbances obtained after removing the discs and subtracting the reagent blank.

TABLE 8

| pg DNA | With SB-16 | Without SB-16 |
|---|---|---|
| 0 | 0.026 | 0.435 |
| 0.1 | 0.050 | 0.417 |
| 1.0 | 0.057 | 0.460 |
| 10.0 | 0.151 | 0.523 |

It can be seen that SB-16 greatly reduces the nonspecific binding of alkaline phosphatase/avidin conjugate to nitrocellulose.

I claim:

1. A biochemical detection method in which a ligand is bound to a surface, an aqueous solution containing an antiligand is brought into contact therewith whereby antiligand becomes bound to ligand, the aqueous solution is separated from the thus bound antiligand, and the antiligand is detected using a detection means associated therewith, wherein the ligand/antiligand combination on the surface is treated with at least one agent for limiting non-specific binding of either the ligand or the antiligand, which agent is
   (i) a surfactant containing an aromatic residue and having an HLB number of at least 16,
   (ii) a zwitterionic surfactant, or
   (iii) a solution containing a salt of a polyvalent anion, in a concentration of at least 100 mM.

2. A method as claimed in claim 1, wherein the said agent is a compound of the formula Ar-$(OCH_2CH_2)_n$-OA, wherein Ar is a phenyl group optionally substituted by one or more alkyl groups containing in total from 1 to 14 carbon atoms, n is from 20 to 100, and A is a hydrogen atom, or a methyl or ethyl group.

3. A method as claimed in claim 2, wherein the group Ar is a phenyl group, substituted by an alkyl group containing from 4 to 12 carbon atoms.

4. A method as claimed in claim 2, wherein A is hydrogen.

5. A method as claimed in claim 2, wherein n has a value of from 25 to 80.

6. A method as claimed in claim 1, wherein the zwitterionic surfactant is a compound of the formula $R^1R^2NR^3R^4$ wherein $R^1$ and $R^2$ are each independently a $C_1$-$C_6$ alkyl group, $R^3$ is a $C_1$-$C_6$ alkyl group bearing an $SO_3$ substituent, and $R^4$ is a $C_8$-$C_{22}$ alkyl group.

7. A method as claimed in claim 6, wherein $R^1$ and $R^2$ are each a methyl group.

8. A method as claimed in claim 6 or claim 7, wherein $R^3$ is a group of the formula $CH_2CH_2CH_2SO_3H$ 9. A method as claimed in claim 1, wherein the surface is treated with at least one agent for limiting nonspecific binding, which is a solution containing a salt of a polyvalent anion, in a concentration of from 200 to 600 mM.

10. A method as claimed in claim 9, wherein the polyvalent anion is $SO_4^{2-}$.

11. A method as claimed in claim 9, wherein the polyvalent anion is used in a concentration of about 400 mM.

12. A method as claimed in claim 1, wherein at least one agent selected from group (iii) is utilized together with at least one agent selected from group (i) or group (ii).

13. A method as claimed in claim 12, wherein at least one agent from each of the said groups (i), (ii), and (iii) is utilized.

14. A method as claimed in claim 1, wherein the treatment of the surface with said at least one agent is carried out by including said at least one agent in at least one of the aqueous solutions containing the antiligand, and a solution utilized for washing said surface after treatment with said aqueous solution.

15. A biological test kit, comprising a first vessel for containing a test liquid, having a surface therein which is covered by the test liquid when in use, and having a first ligand adapted to bind with a corresponding antiligand, bound to said surface,
   a second vessel containing a reagent solution adapted to bind with antiligand bound with said first ligand,
   and a third vessel containing a washing solution for washing said first vessel,
   wherein the reagent solution or the washing solution contains an agent for limiting nonspecific binding of the ligand or antiligand, which is
   (i) a surfactant containing an aromatic residue and having an HLB number of at least 16,
   (ii) a zwitterionic surfactant, or
   (iii) a solution containing a salt of a polyvalent anion, in a concentration of at least 100 mM.

16. A biochemical detection method in which a ligand is bound to a surface, an aqueous solution containing an antiligand is brought into contact therewith whereby antiligand becomes bound to ligand, the aqueous solution is separated from the thus bound antiligand, and the antiligand is detected using detection means associated therewith, wherein the ligand/antiligand combination on the surface is treated with at least one agent for limiting non-specific binding of either the ligand or the antiligand, which agent is a zwitterionic surfactant having one amine residue and one acidic residue.

17. A biochemical detection method comprising the steps of:
   contacting an aqueous solution containing an antiligand with a surface having a ligand bound thereto, whereby antiligand binds to ligand to form a complex;
   treating the ligand/antiligand combination on the surface with at least one agent for limiting non-specific binding of either the ligand or the antiligand said agent being selected from the group consisting of:
   (i) a surfactant containing an aromatic residue and having an HLB number of at least 16;
   (ii) a zwitterionic surfactant; and
   (iii) a solution containing a salt of polyvalent anion, in a concentration of at least 100 mM;
   separating the aqueous solution from the complex; and
   detecting the antiligand using a detection means.

* * * * *